(12) United States Patent
Mertens (10) Patent No.: US 8,853,117 B2
(45) Date of Patent: Oct. 7, 2014

(54) METHOD OF MAKING A MOLECULAR SIEVE OF MFS FRAMEWORK TYPE WITH CONTROLLABLE AVERAGE SIZE

(75) Inventor: Machteld Maria Wilfried Mertens, Boortmeerbeek (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 243 days.

(21) Appl. No.: 13/388,331

(22) PCT Filed: Aug. 18, 2010

(86) PCT No.: PCT/EP2010/005168
§ 371 (c)(1),
(2), (4) Date: Apr. 12, 2012

(87) PCT Pub. No.: WO2011/023360
PCT Pub. Date: Mar. 3, 2011

(65) Prior Publication Data
US 2012/0190896 A1      Jul. 26, 2012

(30) Foreign Application Priority Data

Aug. 28, 2009   (EP) .................................... 09168922

(51) Int. Cl.
*B01J 29/06*      (2006.01)
*B01J 29/70*      (2006.01)

(52) U.S. Cl.
CPC .............. *B01J 29/7026* (2013.01); *B01J 29/06* (2013.01)
USPC ................... 502/71; 502/60; 502/61; 502/63; 502/240; 502/243

(58) Field of Classification Search
CPC .............................. B01J 29/7026; B01J 29/06
USPC ........................... 502/60, 61, 63, 71, 240, 243
See application file for complete search history.

(56) References Cited

U.S. PATENT DOCUMENTS

| 4,873,067 A | 10/1989 | Valyocsik et al. |
| 4,973,781 A | 11/1990 | Valyocsik et al. |
| 5,672,800 A | 9/1997 | Mathys et al. |
| 6,143,942 A | 11/2000 | Verrelst et al. |
| 6,821,503 B1 * | 11/2004 | Verduijn et al. .............. 423/709 |
| 6,875,899 B2 | 4/2005 | Martens et al. |
| 7,011,810 B2 | 3/2006 | Dakka et al. |
| 7,264,789 B1 | 9/2007 | Verduijn et al. |
| 2007/0191663 A1 * | 8/2007 | Johnson et al. ............... 585/533 |

FOREIGN PATENT DOCUMENTS

| EP | 0 174 121 | 2/1992 |
| EP | 1 105 346 | 5/2008 |
| WO | 00/06494 | 2/2000 |
| WO | 01/83407 | 11/2001 |
| WO | 03/029144 | 4/2003 |
| WO | 2007/094949 | 8/2007 |

OTHER PUBLICATIONS

Lok et al., "The Role of Organic Molecules in Molecular Sieve Synthesis", Zeolites, vol. 3, Oct. 1983, pp. 282-291.
Lee, Song-Ho et al., "Synthesis of Zeolite ZSM-57 and its Catalytic Evaluation for the 1-Butene Skeletal Isomerization and n-Octane Cracking", Journal of Catalysis, vol. 196, No. 1, Nov. 15, 2000, pp. 158-166.
Ernst, S. et al., "Zeolite ZSM-57: Synthesis, Characterization and Shape Selective Properties", Studies in Surface Science and Catalysis, vol. 65, 1991, pp. 645-652.

* cited by examiner

*Primary Examiner* — Sudhakar Katakam
*Assistant Examiner* — Pancham Bakshi
(74) *Attorney, Agent, or Firm* — Darryl M. Tyus (57) ABSTRACT

A method of making a crystalline molecular sieve of MFS framework type, preferably ZSM-57, from a synthesis mixture comprising at least one source of tetravalent element (Y), at least one source of trivalent element (X), at least one source of alkali metal hydroxide (MOH), at least one structure-directing-agent (R) and water, said alkali metal (M) comprising potassium, and having the following mole composition (expressed in terms of oxide):

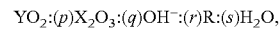

$YO_2:(p)X_2O_3:(q)OH^-:(r)R:(s)H_2O$, wherein (p) is in the range from 0.005 to 0.05, (q) is in the range from 0.01 to 3, (r) is in the range from 0.03 to 2 and (s) is in the range from 10 to 75 (based on total weight of said synthesis mixture); wherein the crystals of molecular sieve formed having an average diameter (D) of less than or equal to 1.5 micron and an average thickness (T) of less than or equal to 300 nanometers.

10 Claims, 8 Drawing Sheets

METHOD OF MAKING A MOLECULAR SIEVE OF MFS FRAMEWORK TYPE WITH CONTROLLABLE AVERAGE SIZE

CROSS REFERENCE TO RELATED APPLICATIONS

This application is a National Stage Application of International Application No. PCT/EP2010/005168, filed Aug. 18, 2010, which claims the benefit of prior European Patent Application No. 09168922.4, filed Aug. 28, 2009, both of which are hereby incorporated by reference in their entireties.

FIELD OF THE INVENTION

This invention relates to a method of making a crystalline molecular sieve of MFS framework type, preferably ZSM-57, having controllable size and to its use in catalytic conversion of organic compounds.

BACKGROUND OF THE INVENTION

Molecular sieves of the MFS framework type, and in particular ZSM-57, are useful catalyst components for a variety of conversion processes, such as hydrocarbon cracking, dehydrogenation, oligomerization, isomerization, disproportionation, and alkylation as well as the formation of hydrocarbons from oxygen-containing compounds such as alcohols and ethers. See U.S. Pat. Nos. 5,672,800; 6,143,942; 6,875,899 and International Application Publication WO 01/83407.

The composition, properties and preparation of ZSM-57 are disclosed in European Patent 174,121, U.S. Pat. Nos. 4,873,067 and 4,973,781, and International Application Publication WO 03/029144 and WO2007/094949, the entire disclosures of these documents being incorporated by reference herein. ZSM-57 is a zeolite with a typical molar ratio of $YO_2:X_2O_3$ of at least 4, wherein Y represents silicon and/or germanium and X represents aluminum, and/or boron, and/or chromium, and/or iron, and/or gallium. Preferably, there are from greater than 8 to about 200 moles of $YO_2$ per mole of $X_2O_3$. Preferably, $YO_2$ is silica and $X_2O_3$ is alumina.

ZSM-57 may be prepared as described in European Patent 174,121 from a synthesis mixture containing sources of alkali metal ions, an oxide of silicon, an oxide of aluminum, water and an organic directing agent which is a salt of N,N,N,N',N',N'-hexaethylpentane diammonium (HEPD, also known as hexaethyl-Diquat-5), and maintaining said mixture under crystallization conditions until the required zeolite is formed. The synthesis mixture has a composition within the following ranges: $SiO_2:Al_2O_3$ of 20 to 200:1, preferably 40 to 100:1; $H_2O:SiO_2$ of 10 to 200:1, preferably of 20 to 50:1; $OH^-:SiO_2$ of 0 to 3:1, preferably 0.1 to 0.5:1; $Z:SiO_2$ of 0 to 3:1, preferably of 0.1 to 2:1, where Z is an alkali metal cation; $R:SiO_2$ of 0.01 to 2:1, preferably of 0.1:1, where R is HEPD, preferably its dibromide salt. Crystallization of zeolite ZSM-57 may be carried out under either static or stirred conditions. A useful range of temperatures for crystallization is from 80° C. to 350° C. for a time of 12 hours to 200 days. Thereafter, the crystals are separated from the liquid and recovered. The synthesis of the zeolite crystals is said to be facilitated by the presence of at least 0.01 wt percent, preferably 0.10 wt %, and still more preferably 1 wt %, seed crystals (based on total weight of the synthesis mixture).

U.S. Pat. No. 4,873,067 further illustrates the preparation of boron, chromium, iron and/or gallium-containing zeolite ZSM-57 by a method comprising preparing a mixture containing sources of alkali metal ions, an oxide of silicon, an oxide of aluminum, a source of boron, and/or chromium, and/or iron and/or gallium, water and HEPD, and maintaining said mixture under crystallization conditions until the required zeolite is formed.

U.S. Pat. No. 4,973,781 discloses a synthetic porous zeolite, identified as ZSM-57 based on its characteristic X-ray diffraction pattern, having a molar ratio of $XO_2:Y_2O_3$ of at least 4, wherein X represents silicon and/or germanium and Y represents aluminum, boron, chromium, iron and/or gallium. The silica/alumina form of this crystalline material has a silica to alumina ratio of at least 4 and may be prepared with directing agents which are N,N,N,N',N',N'-hexaethylpentane-diammonium compounds.

International Application Publication WO 03/029144 and U.S. Pat. No. 7,011,810 disclose a process for the manufacture of a crystalline molecular sieve of the MFS framework type, which comprises hydrothermal treatment of a synthesis mixture containing sources of alkali metal ions, of aluminum, and of silicon, water, an N,N,N,N',N',N'-hexaethylpentane diammonium salt (HEPD), hereinafter R1, and R2, an amine of formula $NR^1R^2R^3$ or a quaternary ammonium compound of formula $R^1R^2R^3R^4NX$, wherein $R^1$, $R^2$, $R^3$, or $R^4$, which may be identical or different, each independently represent a hydrogen atom, a linear alkyl group having from 1 to 8 carbon atoms, a branched alkyl group having from 3 to 8 carbon atoms, or a cycloalkyl group having 5 or 6 carbon atoms, at least one of $R^1$, $R^2$, $R^3$, and if present $R^4$, being other than hydrogen, and X represents an anion.

International Application Publication WO2007/094949 discloses a method of making a crystalline molecular sieve of MFS framework type at lower alkalinity and water content, such method comprises the steps of (a) adding at least one source of ions of tetravalent element (Y), at least one source of ions of trivalent element (X), at least one hydroxide source (OH), at least one structure-directing-agent (R), at least one seed source (Seed), and water ($H_2O$) to form a mixture having the following mole composition (expressed in term of oxide): $YO_2:(n)X_2O_3:(x)OH^-:(y)R:(z)H_2O+(m)Seed$ wherein the m is in the range of from about 10 wtppm to about 2 wt. % (based on total weight of the synthesis mixture), the n is in the range of from about 0.005 to 0.05, the x is in the range of from about 0.01 to about 0.3, the y is in the range of from about 0.03 to about 2; and the z is in the range of from about 3 to about 30; and (b) treating said mixture under crystallization conditions to form said crystalline molecular sieve substantially free of non-MFS material, wherein said crystallization conditions comprise a temperature in the range of from about 150° C. to about 250° C., a crystallization time of less than or equal to 100 hr, and a weight hourly throughput of at least $0.001\ hr^{-1}$.

While changing the alkalinity and water content of the zeolite synthesis mixture allows for optimization of the synthesis yield, it does not have a significant impact on the crystal size or the morphology of the resultant crystalline molecular sieves of MFS framework type, such as ZSM-57. Crystal size is an important property of molecular sieves. The ability to control crystal size (i.e., the average diameter and/or average thickness) of the crystal provides the ability to fine-tune a molecular sieve for specific applications in catalysis and molecular separations. Therefore, there is a need for a method to control the crystal size and/or the morphology of MFS framework type molecular sieves, such as ZSM-57. We have now found that the average diameter and/or the average thickness of the crystalline molecular sieve of MFS framework type may be modified when the water content of the synthesis mixture is controlled and the synthesis takes place in the presence of potassium with or without sodium according to the methods disclosed herein. Also, the crystals formed in the absence of sodium have a different morphology with more pronounced edges and a more regular surface texture.

SUMMARY OF THE INVENTION

In one embodiment, this invention relates a method of making a crystalline molecular sieve of MFS framework type, said method comprising the steps of:

(a) providing a synthesis mixture comprising at least one source of tetravalent element (Y), at least one source of trivalent element (X), at least one source of alkali metal hydroxide (MOH), at least one structure-directing-agent (R) and water, said alkali metal (M) comprising potassium, said mixture having the following molar composition (expressed in terms of oxide):

$$YO_2:(p)X_2O_3:(q)MOH:(r)R:(s)H_2O$$

wherein (p) is in the range from 0.005 to 0.05, (q) is in the range from 0.01 to 3, (r) is in the range from 0.03 to 2 and (s) is in the range from 10 to 75; and (b) treating said synthesis mixture under crystallization conditions to form crystals of molecular sieve of MFS framework type, said crystals having an average diameter (D) of less than or equal to 1.5 micron and an average thickness (T) of less than or equal to 300 nanometers. Preferably, said crystallization conditions comprise a temperature in the range from 150° C. to 250° C. and a crystallization time of less than or equal to 100 hr. Preferably, the tetravalent element is silicon (Si). Preferably, the trivalent element is aluminum (Al), gallium (Ga), and mixtures thereof.

Preferably, the crystalline molecular sieve of MFS framework type is ZSM-57.

Preferably, said average diameter (D) of crystals of the molecular sieve is in the range from 0.4 to 1.3 microns, and said average thickness (T) is in the range from 40 to 200 nanometers.

Preferably, the at least one alkali metal (M) is potassium or mixtures of sodium and potassium. When said alkali metal (M) is a mixture of sodium ($q_1$) and potassium ($q_2$), the molar ratio of sodium ($q_1$) divided by the molar ratio of potassium ($q_2$) in the synthesis mixture is less than or equal to 2.0.

In an embodiment, this invention relates to a process for hydrocarbon conversion comprising the step of contacting the hydrocarbon with a crystalline molecular sieve of MFS framework type manufactured by the method disclosed in the preceding paragraphs.

In yet another embodiment, this invention relates to crystalline molecular sieves of the MFS framework type having specific average diameters (D) and average thicknesses (T).

These and other embodiments of the present invention shall become apparent from the following detailed description, figures, and appended claims.

DETAILED DESCRIPTION OF THE INVENTION

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

As used in this specification, the term "average diameter" means the numerical average of the longest dimension viewed from the top of at least 20 dried, as-synthesized solid crystals as measured from SEM images of the same magnification level.

As used in this specification, the term "average thickness" means the numerical average of the widest dimension viewed from the side of at least 20 crystals as measured from SEM images of the same magnification level.

As used in this specification, the term "framework type" is used in the sense described in the "Atlas of Zeolite Framework Types," eds. Ch. Baerlocher, W. H. Meier, and D. H. Olson, Elsevier, Fifth Edition, 2001, which is hereby incorporated by reference.

Synthetic zeolites are often prepared from aqueous synthesis mixtures comprising sources of appropriate oxides. Organic directing agents may also be included in the synthesis mixture for the purpose of influencing the production of a zeolite having the desired structure. The use of such directing agents is discussed in an article by Lok et al. entitled "The Role of Organic Molecules in Molecular Sieve Synthesis" appearing in Zeolites, Vol. 3, October, 1983, pp. 282-291.

The invention provides a method of making a crystalline molecular sieve of the MFS framework type, preferably ZSM-57, having controlled average diameter (D) and/or average thickness and morphology, which comprises the steps of providing a synthesis mixture having a composition within the molar ranges (expressed in terms of oxide) under crystallization conditions:

| | |
|---|---|
| 0.005 to 0.5 | $X_2O_3:YO_2$ |
| 0.01 to 3 | $MOH:YO_2$ |
| 10 to 75 | $H_2O:YO_2$ |
| 0.03 to 2 | $R:YO_2$ | wherein M represents an alkali metal ion, R represents a structure-directing-agent, X represents a trivalent element and Y represents a tetravalent element.

Preferred molar ranges are:

| | |
|---|---|
| 0.01 to 0.5 | $X_2O_3{:}YO_2$ |
| 0.1 to 0.5, preferably 0.05 to 0.25 | $MOH{:}YO_2$ |
| 10 to 60 | $H_2O{:}YO_2$ |
| 0.05 to 1 | $R{:}YO_2$ |

Alkali Metal

In the present synthesis method, the alkali metal (M) is selected from the group consisting of sodium, potassium and mixtures of sodium and potassium. Preferably, the alkali metal (M) comprises potassium, more preferably a mixture of potassium and sodium. The sodium source may be sodium hydroxide or sodium aluminate. The potassium source may be potassium hydroxide. In embodiments when the alkali metal (M) is a mixture of sodium and potassium, the molar ratio of sodium ($q_1$) divided by the molar ratio of potassium ($q_2$) in said synthesis mixture is less than or equal to 2.0; or less than or equal to 1.0; preferably, in the range from 0.25 to 2.0; and conveniently, in the range from 0.1 to 0.5.

The molar ratio of alkali metal (M) relative to $YO_2$ in the synthesis mixture, expressed in terms of oxide, q, is typically in the range from 0.03 to 2, preferably from 0.05 to 0.25, more preferably from 0.05 to 2, even more preferably from 0.1 to 1, such as from 0.15 to 0.5. Conveniently it is in the range from 0.01 to 0.5.

Water Ratio

The molar ratio of water relative to $YO_2$ in the synthesis mixture, expressed in terms of oxide, s, is typically in the range from 10 to 75, such as from 10 to 70, preferably from 10 to 65, more preferably from 10 to 60, and even more preferably from 10 to 50.

Average Size Control

We surprisingly found that the average diameter and/or average thickness of the crystalline molecular sieve of MFS framework type may be modified when the water content of the synthesis mixture is controlled and the synthesis takes place in the presence of potassium with or without sodium according to the method disclosed herein. A more concentrated synthesis mixture increases both the average diameter and the average thickness of the crystals produced.

In one or more embodiments, the crystals of molecular sieve of MFS framework type have an average diameter (D) of less than or equal to 1.5 micron, preferably in the range from 0.4 to 1.3 micron, more preferably from 0.6 to 1.3 micron, conveniently from 0.4 to 1.3 micron. Alternatively, the crystals of molecular sieve of MFS framework type have an average diameter (D) in the range from 0.4 to 0.6 microns. In yet another alternative embodiment, the crystals of molecular sieve of MFS framework type have an average diameter (D) in the range from 0.1 to 0.6 microns, such as from 0.2 to 0.5 or from 0.3 to 0.4.

In one or more embodiments, the crystals of molecular sieve of MFS framework type have an average thickness (T) of less than or equal to 300 nanometers, preferably in the range from 40 to 250 nanometers, such as from 40 to 200 nanometers, more preferably in the range from 40 to 150 nanometers, even more preferably in the range from 40 to 100 nanometers. Alternatively, the crystals of molecular sieve of MFS framework type have an average thickness (T) in the range from 100 to 250 nanometers, such as in the range from 100 to 200 nanometers, or in the range from 125 to 200 nanometers, such as in the range from 150 to 175 nanometers.

The above-mentioned average diameter (D) and average thickness (T) ranges may vary independently of each other, depending on the specific synthesis conditions chosen.

In one or more embodiments, the crystals of molecular sieve of MFS framework type have a specified average diameter (D) in combination with a specified average thickness (T). In particular, the specified average diameter (D) of less than or equal to 1.5 micron or in the range from 0.4 to 1.3 micron, more preferably in the range from 0.4 to 0.6 microns or more preferably in the range from 0.6 to 1.3 microns, may be combined with an average thickness (T) of less than or equal to 300 nanometers or in the range from 40 to 200 nanometers, more preferably in the range from 40 to 100 nanometers or more preferably in the range from 100 to 200 nanometers.

The invention thus also relates to crystalline molecular sieves of the MFS framework type having specific average diameters (D) and average thicknesses (T). Non-limiting examples of preferred crystalline molecular sieves of the MFS framework type prepared according to this invention include crystalline molecular sieves of the MFS framework type, in which:

the average diameter (D) is in the range from 0.4 to 1.3 microns and the average thickness (T) is in the range from 40 to 200 nanometers; or the average diameter (D) is in the range from 0.4 to 0.6 microns and the average thickness (T) is in the range from 100 to 200 nanometers, preferably in the range from 150 to 200 nanometers; or the average diameter (D) is in the range from 0.6 to 1.3 microns and the average thickness (T) is in the range from 40 to 100 nanometers; or the average diameter (D) is in the range from 0.6 to 1.3 microns and the average thickness (T) is in the range from 100 to 200 nanometers.

the average diameter (D) is in the range from 0.4 to 0.6 microns and the average thickness (T) is in the range from 40 to 100 nanometers.

Directing Agent

The directing agent used in this invention comprises an N,N,N,N',N',N'-hexaethylpentane diammonium salt (HEPD), hereinafter $R_1$, optionally with one or more of a second directing agent, $R_2$. $R_2$ is selected from amines of formula $NR^1R^2R^3$ and quaternary ammonium compounds of formula $R^1R^2R^3R^4NA$, wherein $R^1$, $R^2$, $R^3$ and $R^4$, which may be identical or different, each independently represent a hydrogen atom, a linear alkyl group having from 1 to 8 carbon atoms, a branched alkyl group having from 3 to 8 carbon atoms, or a cycloalkyl group having 5 or 6 carbon atoms, at least one of $R^1$, $R^2$, $R^3$, and if present $R^4$, being other than hydrogen, and A representing an anion. Mixtures of two or more compounds $R_1$ may be used. Mixtures of two or more compounds $R_2$ may also be used. These may be mixtures of two or more amines, or of two or more quaternary compounds, or of one or more amines and one or more quaternary compounds.

When both $R_1$ and $R_2$ are present in the synthesis mixture, the synthesis mixture preferably has a composition within the molar ranges of:

| | |
|---|---|
| 0.005 to 0.5 | $X_2O_3{:}YO_2$ |
| 0.01 to 3 | $MOH{:}YO_2$ |
| 10 to 75 | $H_2O{:}YO_2$ |
| 0.015 to 2 | $R^1{:}YO_2$ |
| 0.015 to 2 | $R^2{:}YO_2$ |
| 0.03 to 2 | $(R^1+R^2){:}YO_2$ |

In some embodiments, the amines that may be used as the second organic directing agent $R_2$, include, for example, mono, di- and tri-methylamine, mono-, di- and triethylamine, mono-, di- and tri propylamines, mono-, di- and trihexylamines, mono-, di- and triheptylamines, mono-, di- and trioctylamines, cyclopentylamine and cyclohexylamine Advantageously, the amine is a triamine, i.e., none of $R^1$, $R^2$, and $R^3$ represents hydrogen. Preferably, the amine of formula $NR^1R^2R^3$ is selected from trimethylamine, triethylamine and a tripropylamine; most preferably it is triethylamine Advantageously, the quaternary ammonium compound corresponds to one of the above amines, and is preferably a tetralkylammonium compound, preferably a tetramethyl-, tetraethyl-, or tetrapropyl-ammonium compound, a tetra ethylammonium compound being most preferred. As examples of the anion there may be mentioned halide, especially chloride or bromide, and hydroxide. Mixtures of these compounds may be used, as indicated above.

Tetravalent Element

In all of the embodiments of this invention, the tetravalent element, includes, but is not limited to, silicon (Si), germanium (Ge), tin (Sn), and mixtures thereof. When $YO_2$ is silica, the silica source may be fumed silica, precipitated silica and colloidal silica, silicon alkoxide and mixtures thereof. The silica source preferably contains about 30 wt. % solid silica, such as silica sold by Degussa Corporation (now known as Evonik Degussa GmbH, Essen, Germany) under the trade names Aerosil or Ultrasil (a precipitated, spray dried silica containing about 90 wt. % silica). Also, an aqueous colloidal suspension of silica, such as one sold by Grace Davison (Columbia, Md., USA) under the trade name Ludox, or HiSil (a precipitated hydrated $SiO_2$ containing about 87 wt. % silica, about 6 wt. % free $H_2O$ and about 4.5 wt. % bound $H_2O$ of hydration and having a particle size of about 0.02 microns) may be used. Preferably, the $YO_2$, e.g., silicon source, contains about 30 wt. % solid $YO_2$ and more preferably about 40 wt. % solid $YO_2$. The source of silicon may also be a silicate, e.g., an alkali metal silicate, or a tetraalkyl orthosilicate. The source of tetravalent element Y preferably comprises solid $YO_2$, preferably about 30 wt. % solid $YO_2$ in order to obtain the crystal product of this invention.

Trivalent Element

In all of the embodiments of this invention, the trivalent element X, includes, but is not limited to, aluminum (Al), boron (B), gallium (Ga), iron (Fe), and mixtures thereof. Preferably, the trivalent element X is aluminum, and the aluminum source is aluminum sulfate, aluminum hydroxide, hydrated alumina and mixtures thereof. Other aluminum sources include, but are not limited to, other water-soluble aluminum salts, sodium aluminate, or an aluminum alkoxide, such as aluminum isopropyloxide, or an aluminum metal, such as aluminum in the form of chips.

Seed Crystals

In some embodiments, the synthesis mixture may contain seed crystal. It is well known that seeding a molecular sieve synthesis mixture frequently has beneficial effects, for example in controlling the particle size of the product, avoiding the need for an organic directing agent, accelerating synthesis, and improving the proportion of product that is of the intended framework type.

The seeds may be obtained from a previous synthesis and be colloidal or near-colloidal. Seeds of a different framework type, especially LEV, may be used. The preparation of colloidal LEV seeds is described in International application WO 00/06494. Seeds are advantageously present in a proportion from 0.0001 wt. % (10 weight part per million or "wtppm") to 2 wt. %, preferably 0.001 wt. % to 1 wt. %, more preferably 0.01 wt. % to 0.5 wt. %, by weight, based on the total weight of synthesis mixture. For certain synthesis mixtures, a pure MFS framework type material is more readily obtained with seeding.

As used herein, the term "colloidal", when used in connection with a suspension, refers to one containing discrete finely divided particles dispersed in a continuous liquid phase. Preferably, a "colloidal suspension" refers to a suspension that is stable, in the sense that no visible separation occurs or sediment forms, in a period sufficient for the use intended, such as for at least 10, or at least 20, or at least 100, or at least 500, hours at ambient temperature (23° C.). The maximum size of the particles for the suspension to remain stable (peptized) will depend to some extent on their shape, and on the nature and pH of the continuous medium, as well as on the period during which the suspension must remain usable. In general, the maximum dimension will be 500, or 400, or 300, or 200, or 100 nm. The particles may be spherical, or of other shapes. Where particles are other than spherical, the dimension referred to is their smallest dimension.

As indicated above, the colloidal seeds have utility in the manufacture of a variety of crystalline molecular sieves by incorporating the seeds as a component of a synthesis mixture. They are advantageously incorporated in the synthesis mixture in the form of a suspension, advantageously in an aqueous medium, preferably water, or another liquid component of the synthesis mixture. Less preferably they may be added in dry or freeze-dried, but preferably not calcined, form. It is believed that calcination significantly reduces the activity of small crystallites to act as seeds; similarly any other treatment that reduces the seeding activity of materials should be avoided.

Crystallization Conditions

In general, the treatment of the synthesis mixture to yield the desired crystalline molecular sieve, usually termed hydrothermal treatment is conveniently carried out under autogenous pressure, for example in an autoclave, which may, if desired, be PTFE-lined.

The hydrothermal treatment may be carried out under conventional molecular sieve synthesis conditions. Advantageously used are temperatures within the range from 100° C. to 250° C., preferably from 150° C. to 200° C., and more preferably from 160° C. to 180° C. Temperature may be increased, gradually or stepwise, during treatment. Advantageously, a time within the range from 1 to less than or equal to 100 hours, preferably from 10 to less than or equal to 72 hours, and conveniently from 20 to less than or equal to 48 hours, is employed, lower temperatures corresponding to longer times.

For certain applications, the treatment is carried out with any type of agitation, e.g., stirring or rotating the vessel about a horizontal axis (tumbling). For other applications, static hydrothermal treatment is preferred. If desired, the synthesis mixture may be stirred or tumbled during an initial part of the heating stage, for example, from room temperature to an elevated, e.g., the final treatment, temperature, and be static for the remainder. Agitation generally produces a product with a smaller particle size and a narrower particle size distribution than static hydrothermal treatment.

It has been found that for certain synthesis mixture compositions, a pure MFS framework type material is more readily obtained when synthesis is carried out with agitation. For a composition that gives pure material whether synthesis is carried out with or without agitation, crystal size is normally greater if the synthesis is carried out without agitation.

The procedure may include an aging period, either at room temperature or at a moderately elevated temperature, lower than that used for the hydrothermal treatment. The latter may include a period of gradual or stepwise variation in temperature.

Organic Conversion

The direct product of the synthesis described above may be calcined, cation-exchanged, and otherwise treated as is known in the art. Alkali metal cations in the as-synthesized or calcined form may be removed, e.g., by treatment with concentrated acids, e.g., HCl, or with a fugitive base, e.g., an ammonium compound, to provide the material in its hydrogen form.

The products of the invention, if required after cation exchange and/or calcining, have utility as catalyst precursors, catalysts, and separation and absorption media. They are especially useful in numerous organic, e.g., hydrocarbon, compound conversions, separations and absorptions. They may be used alone, or in admixture with other molecular sieves, in particulate form, supported or unsupported, or in the form of a supported layer. Hydrocarbon conversions include, for example, cracking, reforming, hydrofining, aromatization, oligomerization (e.g., di- and trimerization, especially of olefins having 3 to 6 carbon atoms, more especially butene trimerization), isomerization, dewaxing, and hydrocracking (e.g., naphtha to light olefins, higher to lower molecular weight hydrocarbons, alkylation, transalkylation, disproportionation or isomerization of aromatics). Other conversions include the reaction of alcohols with olefins and the conversion of oxygenates to hydrocarbons.

EXAMPLES

The following numbered Examples, in which all parts percentages are by weight unless otherwise indicated, illustrate the invention. Percentage yields are based on the total weight of synthesis mixture.

The N,N,N,N',N',N'-hexaethylpentane diammonium dibromide (HEPD dibromide salt, also known as Hexaethyl-Diquat-5 bromide salt) was prepared according to the following procedure:

1 mole of 1,5-dibromopentane and 2 moles of triethylamine were dissolved in ethanol and refluxed overnight. The resulting solution was concentrated and finally evaporated to dryness under vacuum at 35° C. The white product was recrystallized from ether and identified as HEPD dibromide salt. HEPD dibromide salt is hereinafter abbreviated as $R_1$ in the Examples.

The LEV seeds sample was prepared according to the disclosures in International application WO 00/06494, EP1105346 and EP1105348.

The SEM images were obtained on a JEOL JSM-6340F Field Emission Scanning Electron Microscope (from JEOL Ltd., Tokyo, Japan), applying different magnification at a voltage of 2 keV.

The XRD diffraction patterns were recorded on a Stoe Stadi P Diffractometer (from STOE & Cie GmbH, Darmstadt, Germany) in transmission mode, using Cu K-α radiation or on a SCINTAG X2 X-Ray Powder Diffractometer (from Scintag Inc, Cupertino Calif., USA), using Cu K-α radiation.

The crystal dimensions (i.e., diameter and thickness) were estimated by averaging the measured values on at least 20 crystals in several SEM micrograph images of the same sample at the same magnification level.

COMPARATIVE EXAMPLE

A synthesis mixture was prepared containing the following ingredients: [a] A solution made by combining aluminum sulfate hydrate ($Al_2(SO_4)_3 \cdot 18H_2O$) from J. T. Baker, Philipsburg, N.J., USA (hereinafter referred to as "Baker") and NaOH (Baker) in water, boiling until a clear solution is obtained and correcting for the weight loss of water after cooling to room temperature; [b] A solution of HEPD dibromide in water; [c] Ludox HS40, colloidal silica sol from Grace Davison, Columbia, Md., USA, containing 40% of $SiO_2$ in water); and [d] LEV seeds.

First [b] was added to [c] and stirred before [a] was added. Finally [d] was mixed in with the other ingredients. All these ingredients were combined in the appropriate ratio to result in a synthesis mixture with the following molar composition:

0.4NaOH:0.017Al$_2$O$_3$:0.1R$_1$:SiO$_2$:40H$_2$O+175 ppm LEV seeds.

Figure 1A:
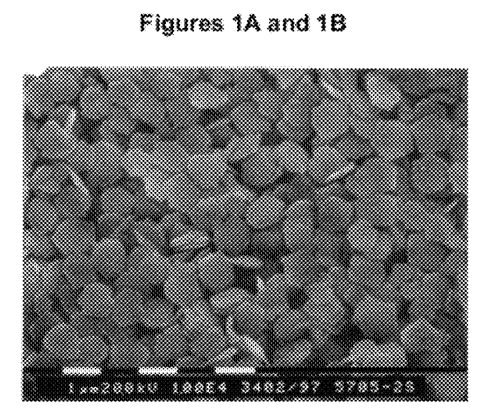
FIGS. 1A and 1B are Scanning Electronic Microscope (SEM) images of the dried as-synthesized solid product of the Comparative Example at 1× and 3× magnification, respectively.
Figure 1B:
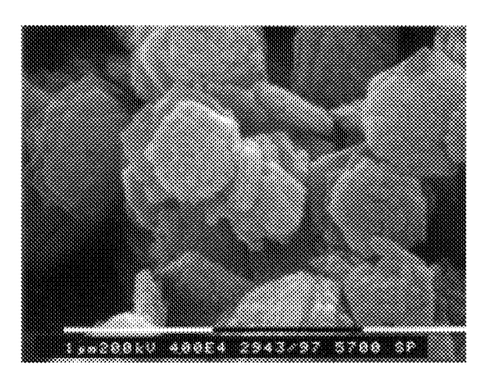

The amount of seeds added is relative to the total weight of the synthesis mixture. The final synthesis mixture was transferred to a stainless steel autoclave and submitted to a hydrothermal treatment under the following conditions: the autoclave was heated up with a rate of 17.5° C./hr to 160° C. and kept at this temperature for 144 hrs under static conditions. After the pre-set time, the autoclave was cooled to room temperature and the resulting solids were separated from the mother liquor and washed several times with demineralized water. The washed solids were dried overnight at 120° C. From the obtained product, the yield was calculated, an XRD pattern was recorded, SEMs were taken and an elemental analysis was performed. The product, obtained with 5.5 wt % yield, expressed as the relative amount of crystals obtained per total synthesis mixture heated, was crystalline and was identified as pure ZSM-57. The Si/Al$_2$ was determined to be 43. The morphology of the crystals, as illustrated in FIGS. 1A and 1B, is platelet with pseudo-pentagonal shape with ill defined edges and with globular surface texture and an average diameter of around 1 μm. The average thickness was roughly estimated at 100 nm.

Example 1

A similar synthesis mixture as in the Comparative Example was prepared but replacing NaOH by KOH. The alumina source was also replaced by Al(OH)$_3$ as supplied by Alcoa Corporation, Pittsburgh, Pa., USA. All the ingredients were combined in the appropriate ratio to result in a synthesis mixture with the following molar composition:

0.4KOH:0.017Al$_2$O$_3$:0.1R$_1$:SiO$_2$:40H$_2$O+162 ppm LEV seeds.

Figure 2A:
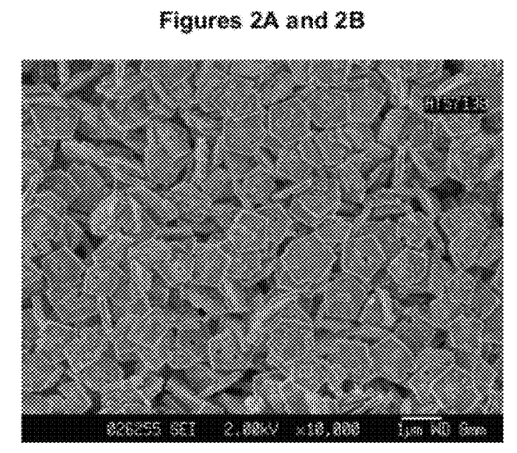
FIGS. 2A and 2B are SEM images of the dried, as-synthesized solid product of Example 1 at 1× and 3× magnification levels, respectively.
Figure 2B:
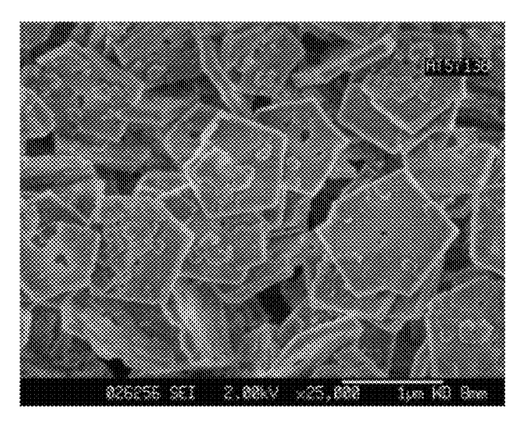

The synthesis mixture was transferred to a stainless steel autoclave and submitted to a hydrothermal treatment under the following conditions: the autoclave was heated in 2 hrs to 160° C. and kept at this temperature for the duration of 144 hrs under static conditions. After the pre-set time, the autoclave was cooled to room temperature and the resulting solids were separated from the mother liquor and washed several times with demineralized water. The washed solids were dried overnight at 120° C. From the obtained product, the yield was calculated, an XRD pattern was recorded and SEMs were taken. The product, obtained with 5.6 wt % yield, was crystalline and was identified as pure ZSM-57. The morphology of the crystals, as illustrated in FIGS. 2A and 2B, is platelet with pseudo pentagonal shape with sharp edges and flaky surface texture and an average diameter of around 1 μm. The average thickness was estimated to be roughly 100 nm.

Example 2

A similar synthesis mixture as in Example 1 was prepared but reducing the H$_2$O/SiO$_2$ ratio to 35. All the ingredients were combined in the appropriate ratios to result in a synthesis mixture with the following molar composition:

0.4KOH:0.017Al$_2$O$_3$:0.1R$_1$:SiO$_2$:35H$_2$O+167 ppm LEV seeds.

Figure 3A:
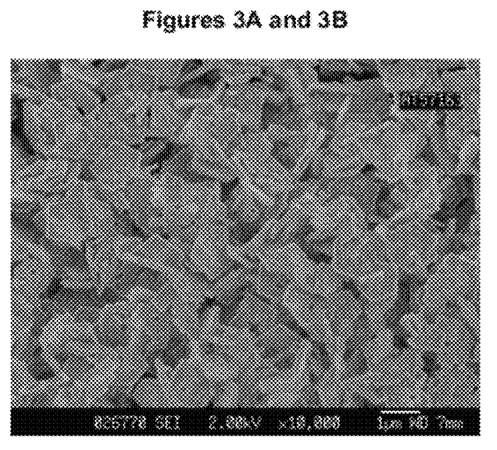
FIGS. 3A and 3B are SEM images of the dried, as-synthesized solid product of Example 2 at 1× and 3× magnification levels, respectively.
Figure 3B:
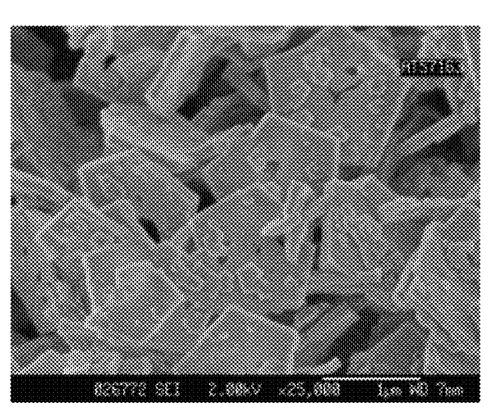

The synthesis mixture was transferred to a stainless steel autoclave and submitted to a hydrothermal treatment under the following conditions: the autoclave was heated in 2 hrs to 160° C. and kept at this temperature for 192 hrs under static conditions. After cooling the autoclave to room temperature, the resulting solids were separated from the mother liquor and washed several times with demineralized water. The washed solids were dried overnight at 120° C. From the obtained product, the yield was calculated, an XRD pattern was recorded and SEMs were taken. The product, obtained with 6.4 wt % yield, was crystalline and was identified as pure ZSM-57. The morphology of the crystals, as illustrated in FIGS. 3A and 3B, is platelet with pseudo pentagonal shape with sharp edges and flaky surface texture and an average diameter of around 1.2 μm. The average thickness was roughly estimated to be 140 nm.

Example 3

A similar synthesis mixture as in Example 1 was prepared but the H$_2$O/SiO$_2$ ratio was increased to 45. All the ingredients were combined in the appropriate ratio's to result in a synthesis mixture with the following molar composition:

0.4KOH:0.017Al$_2$O$_3$:0.1R$_1$:SiO$_2$:45H$_2$O+168 ppm LEV seeds.

Figure 4A:
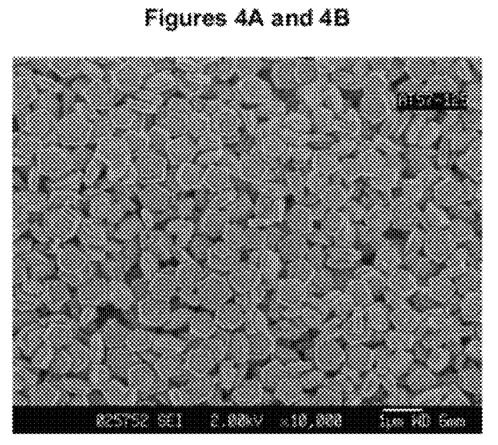
FIGS. 4A and 4B are SEM images of the dried, as-synthesized solid product of Example 3 at 1× and 3× magnification levels, respectively.
Figure 4B:
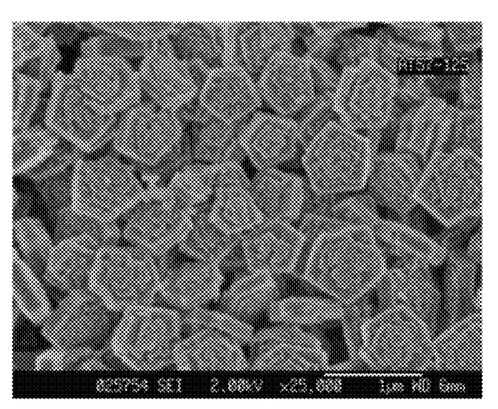

The synthesis mixture was transferred to a stainless steel autoclave and submitted to a hydrothermal treatment under the following conditions: the autoclave was heated in 2 hrs to 160° C. and kept at this temperature for 144 hrs under static conditions. After the pre-set time, the autoclave was cooled to room temperature and the resulting solids were separated from the mother liquor and washed several times with demineralized water. The washed solids were dried overnight at 120° C. From the obtained product, the yield was calculated, an XRD pattern was recorded and SEMs were taken. The product, obtained with 5.2 wt % yield, was crystalline and was identified as pure ZSM-57. The morphology of the crystals, as illustrated in FIGS. 4A and 4B, is platelet with pseudo pentagonal shape with sharp edges and flaky surface texture. The average diameter of the crystals was estimated at 0.7 μm, the average thickness at 160 nm.

Example 4

A similar synthesis mixture as in Example 1 was prepared but with a H$_2$O/SiO$_2$ molar ratio of 50.

All the ingredients were combined in the appropriate ratios to result in a synthesis mixture with the following molar composition:

0.4KOH:0.017Al$_2$O$_3$:0.1R$_1$:SiO$_2$:50H$_2$O+171 ppm LEV seeds.

Figure 5A:
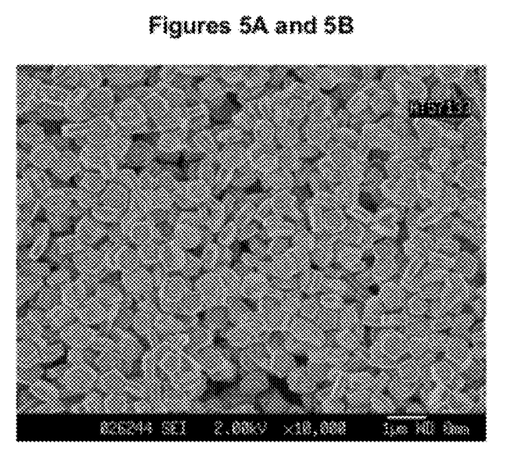
FIGS. 5A and 5B are SEM images of the dried, as-synthesized solid product of Example 4 at 1× and 3× magnification levels, respectively.
Figure 5B:
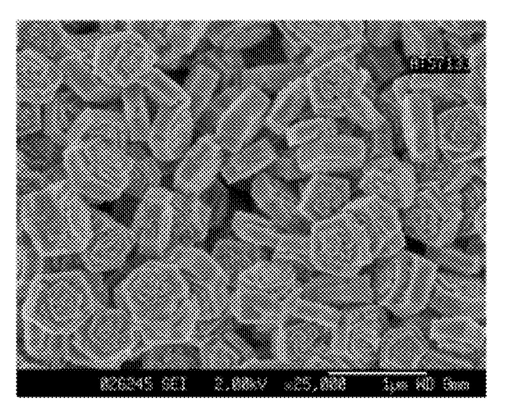

The synthesis mixture was transferred to a stainless steel autoclave and submitted to a hydrothermal treatment under the following conditions: the autoclave was heated in 2 hrs to 160° C. and kept at this temperature for 144 hrs under static conditions. After the pre-set time, the autoclave was cooled to room temperature and the resulting solids were separated from the mother liquor and washed several times with demineralized water. The washed solids were dried overnight at 120° C. From the obtained product, the yield was calculated, an XRD pattern was recorded and SEMs were taken. The product, obtained with 5 wt % yield, was crystalline and was identified as pure ZSM-57. The morphology of the crystals, as illustrated in FIGS. 5A and 5B, is platelet with pseudo pentagonal shape with sharp edges and flaky surface texture and an average diameter of around 0.6 μm. The average thickness was roughly estimated to be 190 nm.

Example 5

A similar synthesis mixture as in Example 1 was prepared but replacing 50% of the KOH by NaOH. All the ingredients were combined in the appropriate ratios to result in a synthesis mixture with the following molar composition:

0.2KOH:0.2NaOH:0.017Al$_2$O$_3$:0.1R$_1$:SiO$_2$:40H$_2$O+ 197 ppm LEV seeds.

Figure 6A:
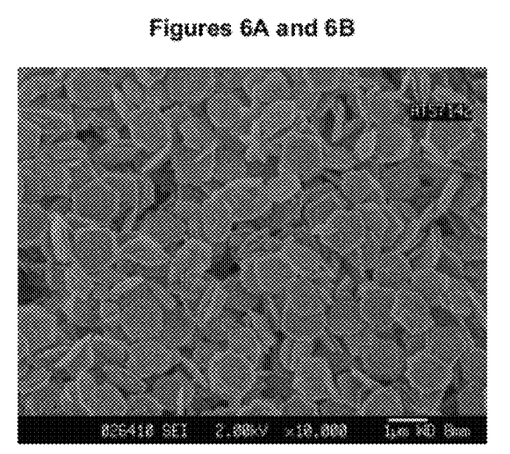
FIGS. 6A and 6B are SEM images of the dried, as-synthesized solid product of Example 5 at 1× and 3× magnification levels, respectively.
Figure 6B:
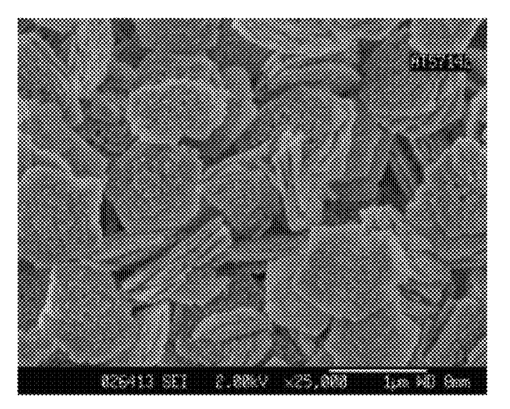

The synthesis mixture was transferred to a stainless steel autoclave and submitted to a hydrothermal treatment under the following conditions: the autoclave was heated in 2 hrs to 160° C. and kept at this temperature for 144 hrs under static conditions. After the pre-set time, the autoclave was cooled to room temperature and the resulting solids were separated from the mother liquor and washed several times with demineralized water. The washed solids were dried overnight at 120° C. From the obtained product, the yield was calculated, an XRD pattern was recorded and SEMs were taken. The product, obtained with 5.4 wt % yield, was crystalline and was identified as pure ZSM-57. The morphology of the crystals, as illustrated in FIGS. 6A and 6B, is platelet with pseudo pentagonal shape and globular surface texture, much like the product of the comparative Example, but thinner. The average diameter was estimated at around 1 μm. The average thickness was roughly 60 nm.

Example 6

Figures 7A, 7B:
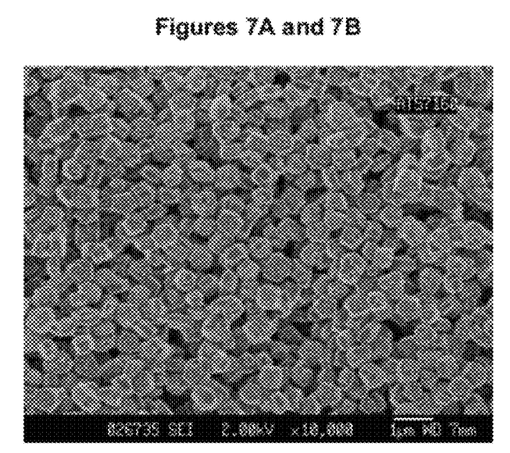
FIGS. 7A and 7B are SEM images of the dried, as-synthesized solid product of Example 6 at 1× and 3× magnification levels, respectively.
Figure 7B:
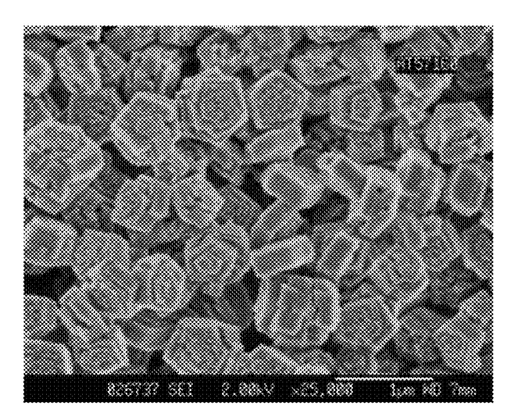

A similar synthesis mixture as in Example 5 was prepared but reducing the alkalinity by 25% with a KOH/NaOH molar ratio of 0.5. All the ingredients were combined in the appropriate ratios to result in a synthesis mixture with the following molar composition: 0.2 KOH: 0.1 NaOH: 0.017 Al$_2$O$_3$:0.1 R$_1$:SiO$_2$: 40 H$_2$O-198 ppm LEV seeds. The synthesis mixture was transferred to a stainless steel autoclave and submitted to a hydrothermal treatment under the following conditions: the autoclave was heated in 2 hrs to 160° C. and kept at this temperature for 144 hrs under static conditions. After the pre-set time, the autoclave was cooled to room temperature and the resulting solids were separated from the mother liquor and washed several times with demineralized water. The washed solids were dried overnight at 120° C. From the obtained product, the yield was calculated, an XRD pattern was recorded and SEMs were taken. The product, obtained with 6.5 wt % yield, expressed as the relative amount of crystals obtained per total synthesis mixture heated, was crystalline and was identified as pure ZSM-57. The morphology of the crystals, as illustrated in FIGS. 7A and 7B, is platelet with pseudo pentagonal shape and flaky surface texture. The average diameter was estimated at around 0.5 μm. The average thickness was roughly 200 nm.

Example 7

The synthesis mixture was prepared in the following way: To a solution of NaOH was added a freshly prepared sodium aluminate and a freshly prepared potassium aluminate solution. These were prepared by combining aluminum trihydroxide [from Alcoa] with respectively NaOH and KOH in the appropriate amounts. To this mixture was added a 25 wt % solution of the HEPD solution used in the previous Examples and a 50 wt % solution of tetraethyl ammonium bromide [$R_2$], as supplied by Sigma-Aldrich Co., St. Louis, Mo., USA. Than the seeds were added and finally, after making the mixture homogeneous, the silica source Ultrasil VN 35P was mixed in. The ingredients were combined in the appropriate ratio's to result in a mixture with the following molar composition:

0.11KOH:0.11NaOH:0.018$Al_2O_3$:0.0246$R_1$: 0.0246$R_2$:$SiO_2$:20$H_2O$+0.2 w % LEV seeds.

Figure 8:
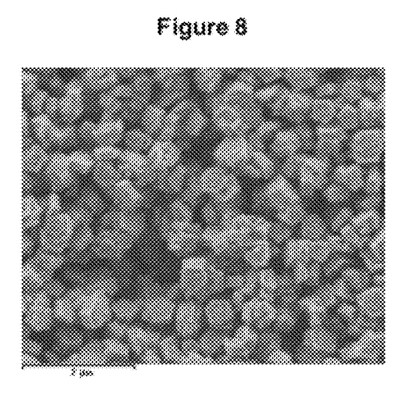
FIG. 8 is a SEM image of the dried, as-synthesized solid product of Example 7 at 1× magnification level.

The synthesis mixture was transferred to a stainless steel autoclave and submitted to a hydrothermal treatment under the following conditions: the autoclave was heated in with a heat-up rate of 25° C./hr to 160° C. and kept at this temperature for 96 hrs under static conditions. After the pre-set time, the autoclave was cooled to room temperature and the resulting solids were separated from the mother liquor and washed several times with demineralized water. The washed solids were dried overnight at 120° C. From the obtained product, the yield was calculated, an XRD pattern was recorded and SEMs were taken. The product, obtained with 12.9 wt % yield, was crystalline and was identified as pure ZSM-57. The morphology of the crystals, as illustrated in FIG. 8, is platelet with pseudo pentagonal shape and flaky surface texture. The average diameter was estimated at around 0.5 μm. The average thickness was roughly 200 nm.

TABLE 1

| Example | $NaOH/SiO_2$ [molar ratio] | $KOH/SiO_2$ [molar ratio] | $H_2O/SiO_2$ [molar ratio] | Yield [wt %] | Average Diameter [μm] | Average Thickness [nm] | Morphology* |
|---|---|---|---|---|---|---|---|
| Comparative | 0.4 | — | 40 | 5.5 | 1 | 100 | A |
| 1 | — | 0.4 | 40 | 5.6 | 1 | 100 | B |
| 2 | — | 0.4 | 35 | 6.4 | 1.2 | 140 | B |
| 3 | — | 0.4 | 45 | 5.2 | 0.7 | 160 | B |
| 4 | — | 0.4 | 50 | 5.0 | 0.6 | 190 | B |
| 5 | 0.2 | 0.2 | 40 | 5.4 | 1 | 60 | A |
| 6 | 0.1 | 0.2 | 40 | 6.5 | 0.5 | 200 | B |
| 7 | 0.11 | 0.11 | 20 | 12.9 | 0.5 | 200 | B |

*Morphology: platelets with pseudo-pentagonal shape
A: Edges not well defined and globular surface texture
B: Edges well defined and flaky surface texture The results of the Examples are shown in Table I. As can be seen, it was observed that changing the relative ratio of K and Na and water content of the synthesis mixture allows for the control of the average diameter and average thickness. The crystals can also be obtained in high yield by fine-tuning both the overall alkalinity and water content.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention claimed is:

1. A method of making a crystalline molecular sieve of MFS framework type, said method comprising the steps of:
   (a) providing a synthesis mixture comprising at least one source of tetravalent element (Y), at least one source of trivalent element (X), at least one source of alkali metal hydroxide (MOH), at least one structure-directing-agent (R) and water, said alkali metal (M) being a mixture of sodium and potassium, said synthesis mixture having the following molar composition (expressed in terms of oxide):

$YO_2$:(p) $X_2O_3$:(q) MOH:(r)R:(s)$H_2O$ wherein (p) is in the range from 0.005 to 0.05,(q) is in the range from 0.01 to 3, (r) is in the range from 0.03 to 2, (s) is in the range from 10 to 75 and the molar ratio of sodium ($q_1$) divided by the molar ratio of potassium ($q_2$,) is less than or equal to 2.0; and
   (b) treating said synthesis mixture under crystallization conditions to form crystals of molecular sieve of MFS framework type, said crystals having an average diameter (D) of less than or equal to 1.5 micron and an average thickness (T) of less than or equal to 300 nanometers.

2. The method of claim 1, wherein said (q) is in the range from 0.05 to 2.

3. The method of claim 1, wherein said (s) is in the range from 10 to 70.

4. The method of claim 1, wherein said tetravalent element is silicon (Si).

5. The method of claim 1, wherein said trivalent element is selected from the group consisting of aluminum (Al), gallium (Ga), and a mixture of aluminum (Al) and gallium (Ga).

6. The method of claim 1, wherein said structure-directing-agent (R) comprises an N,N,N,N',N',N'-hexaethylpentane diammonium salt ($R_1$).

7. The method of claim 6, wherein said structure-directing-agent R further comprises $R_2$ selected from amines of formula $NR^1R^2R^3$ and quaternary ammonium compounds of formula $R^1R^2R^3R^4NA$, wherein $R^1$, $R^2$, $R^3$ and $R^4$, which may be identical or different, each independently represent a hydrogen atom, a linear alkyl group having from 1 to 8 carbon atoms, a branched alkyl group having from 3 to 8 carbon atoms, or a cycloalkyl group having 5 or 6 carbon atoms, at least one of $R^1$, $R^2$, $R^3$, and if present $R^4$, being other than hydrogen, and A representing an anion, and wherein the synthesis mixture further has the following molar ratios:
   ($R_1$+$R_2$)/$YO_2$ in the range from 0.03 to 2; and
   $R_1$/$YO_2$ in the range from 0.015 to 2; or
   $R_2$/$YO_2$ in the range from 0.015 to 2.

8. The method of claim 1, wherein said synthesis mixture further comprises seeds crystals of LEV framework type.

9. The method of claim 1, wherein:
   (i) said at least one source of tetravalent element (Y) is selected from the group consisting of fumed silica, precipitated silica, colloidal silica, silicon alkoxides and mixtures thereof; and (ii) said at least one source trivalent element (X) is selected from the group consisting of aluminum sulfate, aluminum hydroxide and mixtures thereof.

10. The method of claim 1, wherein said crystalline molecular sieve of MFS framework type is ZSM-57.

* * * * *